US010555764B2

(12) United States Patent
Gregersen et al.

(10) Patent No.: US 10,555,764 B2
(45) Date of Patent: Feb. 11, 2020

(54) INTERBODY SPINAL FUSION IMPLANT HAVING LOCKING ELEMENTS THAT OUTWARDLY DISPLACE FOR LOCKING

(71) Applicant: Innovasis, Inc., Salt Lake City, UT (US)

(72) Inventors: Colin S. Gregersen, Salt Lake City, UT (US); Brandon Walker, Layton, UT (US)

(73) Assignee: Innovasis, Inc., Salt Lake City, UT (US)

( * ) Notice: Subject to any disclaimer, the term of this patent is extended or adjusted under 35 U.S.C. 154(b) by 104 days.

(21) Appl. No.: 15/682,970

(22) Filed: Aug. 22, 2017

(65) Prior Publication Data
US 2019/0059963 A1 Feb. 28, 2019

(51) Int. Cl.
| | | |
|---|---|---|
| *A61B 17/80* | (2006.01) | |
| *A61F 2/44* | (2006.01) | |
| *A61B 17/70* | (2006.01) | |
| *A61B 17/86* | (2006.01) | |
| *A61B 17/88* | (2006.01) | |
| *A61F 2/46* | (2006.01) | |

(52) U.S. Cl.
CPC ...... *A61B 17/8057* (2013.01); *A61B 17/7059* (2013.01); *A61B 17/861* (2013.01); *A61F 2/4455* (2013.01); *A61B 17/8875* (2013.01); *A61F 2/46* (2013.01)

(58) Field of Classification Search
CPC ............ A61B 17/8057; A61B 17/7059; A61B 17/7071; A61B 17/7044; A61B 2017/7073; A61B 2017/7077; A61B 2017/7094; A61F 2/4455; A61F 2002/449; A61F 2002/443; A61F 2002/4435
USPC .......................................... 623/17.11–17.16
See application file for complete search history.

(56) References Cited

U.S. PATENT DOCUMENTS

| | | |
|---|---|---|
| 6,432,106 B1 | 8/2002 | Fraser |
| 6,485,517 B1 | 11/2002 | Michaelson |
| 6,558,423 B1 | 5/2003 | Michaelson |
| 6,682,530 B2 | 1/2004 | Dixon et al. |
| 6,835,206 B2 | 12/2004 | Jackson |
| 6,849,093 B2 | 2/2005 | Michelson |
| 7,033,394 B2 | 4/2006 | Michaelson |
| 7,077,864 B2 | 7/2006 | Byrd, III et al. |
| 7,846,207 B2 | 12/2010 | Lechmann et al. |
| 7,862,616 B2 | 1/2011 | Lechmann et al. |
| 7,875,076 B2 | 1/2011 | Mathieu et al. |
| 8,182,539 B2 | 5/2012 | Tyber et al. |

(Continued)

FOREIGN PATENT DOCUMENTS

| | | |
|---|---|---|
| EP | 2 510 904 A1 | 10/2012 |
| WO | 2000/066044 A1 | 11/2000 |
| WO | 2000/066045 A1 | 11/2000 |

*Primary Examiner* — Matthew J Lawson
(74) *Attorney, Agent, or Firm* — Workman Nydegger

(57) ABSTRACT

An interbody spinal fusion implant includes a body and a faceplate secured to the body. A recess is formed on a front face of the faceplate and is at least partially bounded by an interior surface. A first screw hole and a spaced apart first locking hole pass through the faceplate from interior surface of the recess. A first locking screw has a shaft threaded into the first locking hole. The first locking screw blocks removal of a bone screw from within the first screw hole when the locking screw is in a retracted position.

22 Claims, 10 Drawing Sheets

(56) References Cited

U.S. PATENT DOCUMENTS

| | | | |
|---|---|---|---|
| 8,277,493 B2 | 10/2012 | Farris et al. | |
| 8,282,675 B2 | 10/2012 | Maguire et al. | |
| 8,328,872 B2 | 12/2012 | Duffield et al. | |
| 8,403,986 B2 | 3/2013 | Michelson | |
| 8,454,700 B2 | 6/2013 | Lemoine et al. | |
| 8,709,085 B2 | 4/2014 | Lechmann et al. | |
| 8,715,354 B2 | 5/2014 | Lechmann et al. | |
| 8,764,831 B2 | 7/2014 | Lechmann et al. | |
| 8,814,912 B2 | 8/2014 | Carlson et al. | |
| 8,828,084 B2 | 9/2014 | Aflatoon et al. | |
| 8,882,813 B2 | 11/2014 | Jones et al. | |
| 8,882,814 B2 | 11/2014 | Suh | |
| 9,005,295 B2 | 4/2015 | Kueenzi et al. | |
| 10,258,403 B2 * | 4/2019 | DeFalco | A61B 17/8875 |
| 10,322,006 B2 * | 6/2019 | Bennett | A61F 2/4455 |
| 2009/0210062 A1 | 8/2009 | Thalgott et al. | |
| 2010/0057206 A1 * | 3/2010 | Duffield | A61F 2/442 |
| | | | 623/17.16 |
| 2011/0251689 A1 * | 10/2011 | Seifert | A61F 2/442 |
| | | | 623/17.16 |
| 2013/0023994 A1 * | 1/2013 | Glerum | A61F 2/447 |
| | | | 623/17.16 |
| 2013/0268008 A1 | 10/2013 | McDonough et al. | |
| 2013/0282017 A1 | 10/2013 | Moskowitz et al. | |
| 2014/0243985 A1 | 8/2014 | Lechmann et al. | |
| 2014/0277495 A1 | 9/2014 | Muhanna | |
| 2015/0025635 A1 | 1/2015 | Laubert | |
| 2015/0051704 A1 | 2/2015 | Duffield et al. | |
| 2015/0328005 A1 * | 11/2015 | Padovani | A61F 2/442 |
| | | | 623/17.13 |
| 2017/0215930 A1 * | 8/2017 | Lauf | A61B 17/7059 |

\* cited by examiner though the adjacent vertebra fuse together about the implant so as to preclude any movement between the vertebra.
INTERBODY SPINAL FUSION IMPLANT HAVING LOCKING ELEMENTS THAT OUTWARDLY DISPLACE FOR LOCKING

CROSS-REFERENCE TO RELATED APPLICATIONS

Not applicable.

BACKGROUND OF THE INVENTION

1. The Field of the Invention

The present invention relates to interbody spinal fusion implants and, more specifically, to interbody spinal fusion implants having locking elements that outwardly displace for selectively locking bone screws.

2. The Relevant Technology

The spinal column is made up of spaced apart vertebra that are each separated by a cushioning disc. If a disc ruptures or is otherwise damaged, the adjacent vertebra can press against the spinal cord which can cause pain and loss of mobility. In one approach to treating a damaged disc, at least a portion of the damaged disc is removed and a spinal fusion implant is inserted between the adjacent vertebra. The implant keeps the vertebra separated to prevent the vertebra from pressing on the spinal cord. Eventually, the adjacent vertebra fuse together about the implant so as to preclude any movement between the vertebra.

To help fuse the vertebra together, the implant is formed with a hollow cavity that is manually filled with a bone growth material, such as bone allograft, prior to insertion between the vertebra. The openings on the implant enable the bone allograft to facilitate bone growth between the vertebra.

To help keep the implant properly positioned and stationary as the adjacent vertebra are fusing together, bone screws are passed through the implant and are screwed into the adjacent vertebra. One risk associated with using bone screws is that through movement of the patient, the bone screws can work loose and back out of the implant. The movement of the bone screws can cause the implant to become loose and prevent proper fusing between the vertebra. In addition, a loose bone screw is a risk to a patient as it can create obstructions or damage surrounding bone or tissue.

Various approaches have been used to help lock bone screws to spinal implants. Such approaches, however, have typically suffered from shortcomings such as being ineffective, difficult to use, or having a relatively high risk that all or a portion of the implant will dislodge. Accordingly, what is needed in the art are spinal implants having improved assemblies and methods for locking bone screws to the implants.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
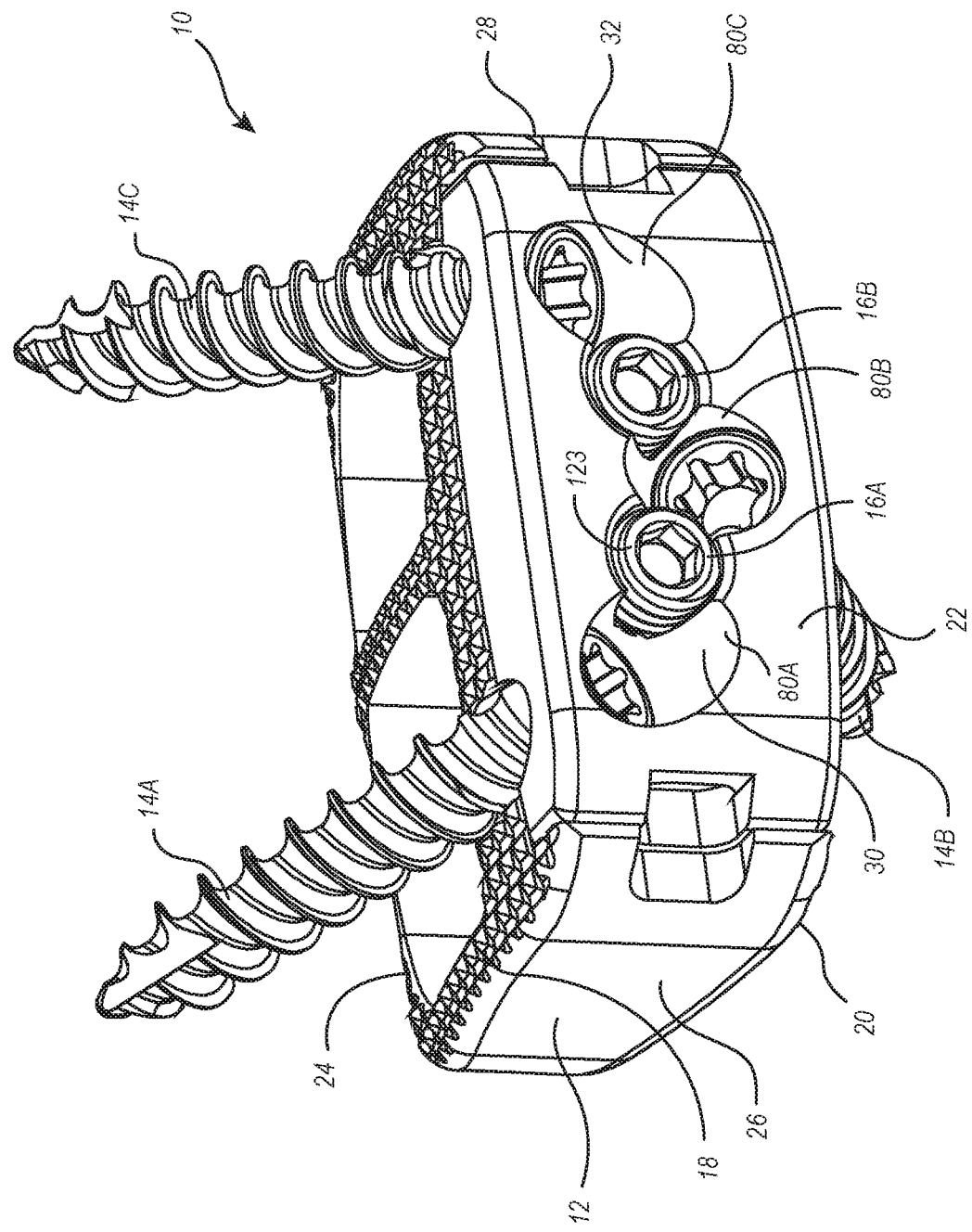
FIG. 1 is a perspective view of an interbody spinal fusion implant incorporating features of the present invention.

Before describing various embodiments of the present disclosure in detail, it is to be understood that this disclosure is not limited to the parameters of the particularly exemplified implants, methods, systems and/or products, which may, of course, vary. Thus, while certain embodiments of the present disclosure will be described in detail, with reference to specific configurations, parameters, features (e.g., components, members, elements, parts, and/or portions), etc., the descriptions are illustrative and are not to be construed as limiting the scope of the claimed invention. In addition, the terminology used herein is for the purpose of describing the embodiments, and is not necessarily intended to limit the scope of the claimed invention.

Unless defined otherwise, all technical and scientific terms used herein have the same meaning as commonly understood by one of ordinary skill in the art to which the present disclosure pertains.

Various aspects of the present disclosure, including implants, systems, processes, and/or products may be illustrated with reference to one or more embodiments or implementations, which are exemplary in nature. As used herein, the terms "embodiment" and "implementation" mean "serving as an example, instance, or illustration," and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

It will be noted that, as used in this specification and the appended claims, the singular forms "a," "an" and "the" include plural referents unless the context clearly dictates otherwise. Thus, for example, reference to a "locking screw" includes one, two, or more locking screws.

As used herein, directional terms, such as "top," "bottom," "left," "right," "up," "down," "upper," "lower," "proximal," "distal," "vertical," "horizontal" and the like are used herein solely to indicate relative directions and are not otherwise intended to limit the scope of the disclosure and/or claimed invention.

Various aspects of the present disclosure can be illustrated by describing components that are bound, coupled, attached, connected, and/or joined together. As used herein, the terms "bound," "coupled", "attached", "connected," and/or "joined" are used to indicate either a direct association between two components or, where appropriate, an indirect association with one another through intervening or intermediate components. In contrast, when a component is referred to as being "directly bound," "directly coupled", "directly attached", "directly connected," and/or "directly joined" to another component, no intervening elements are present or contemplated. Furthermore, binding, coupling, attaching, connecting, and/or joining can comprise mechanical and/or chemical association.

To facilitate understanding, like reference numerals (i.e., like numbering of components and/or elements) have been used, where possible, to designate like elements common to the figures. Specifically, in the exemplary embodiments illustrated in the figures, like structures, or structures with like functions, will be provided with similar reference designations, where possible.

Specific language will be used herein to describe the exemplary embodiments. Nevertheless, it will be understood that no limitation of the scope of the disclosure is thereby intended. Rather, it is to be understood that the language used to describe the exemplar embodiments is illustrative only and is not to be construed as limiting the scope of the disclosure (unless such language is expressly described herein as essential). Furthermore, multiple instances of an element and or sub-elements of a parent element may each include separate letters appended to the element number. An element label with an appended letter can be used to designate an alternative design, structure, function, implementation, and/or embodiment of an element or feature without an appended letter. Likewise, an element label with an appended letter can be used to indicate a sub-element of a parent element. However, element labels including an appended letter are not meant to be limited to the specific and/or particular embodiment(s) in which they are illustrated. In other words, reference to a specific feature in relation to one embodiment should not be construed as being limited to applications only within said embodiment.

Furthermore, multiple instances of the same element may each include separate letters appended to the element number. For example, two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

It will also be appreciated that where multiple possibilities of values or a range a values (e.g., less than, greater than, at least, or up to a certain value, or between two recited values) is disclosed or recited, any specific value or range of values falling within the disclosed range of values is likewise disclosed and contemplated herein.

Depicted in FIG. 1 is one embodiment of an inventive interbody spinal fusion implant 10 incorporating features of the present invention and intended for use in fusing together adjacent vertebra of a spine. In general, fusion implant 10 comprises a fusion spacer 12 having bone screws 14A, 14B, and 14C removably disposed thereon. A pair of locking screws 16A and 16B are adjustably mounted on fusion pacer 12 and are used to prevent unwanted movement or removal of bone screws 14A-C from fusion spacer 12 once fusion spacer 10 has been implanted in the spine. The various elements of fusion implant 10 will now be described in greater detail.

When viewed as a whole, fusion spacer 12 has a top surface 18 and an opposing bottom surface 20 that extend between a front face 22 and an opposing back face 24 and that also extend between opposing side faces 26 and 28. For reference purposes, fusion spacer 12 has a vertical direction extending between top surface 18 and opposing bottom surface 20 and a horizontal or lateral direction extending between opposing side faces 26 and 28. Fusion spacer 12 is wedge-shaped and inwardly tapers from front face 22 to back face 24. Top surface 18 and bottom surface 20 can be linear but typically have a slight convex arch or curve extending from front face 22 to back face 24. Fusion spacer 12 can also be bi-convex with top surface 18 and bottom surface 20 also having slight convex arch or curve extending between opposing side faces 26 and 28. Formed on front face 22 is an elongated recess 30 that extends laterally is at least partially bounded by an interior surface 32. Locking screws 16A and 16B are at least partially disposed within recess 30.

Figure 2:
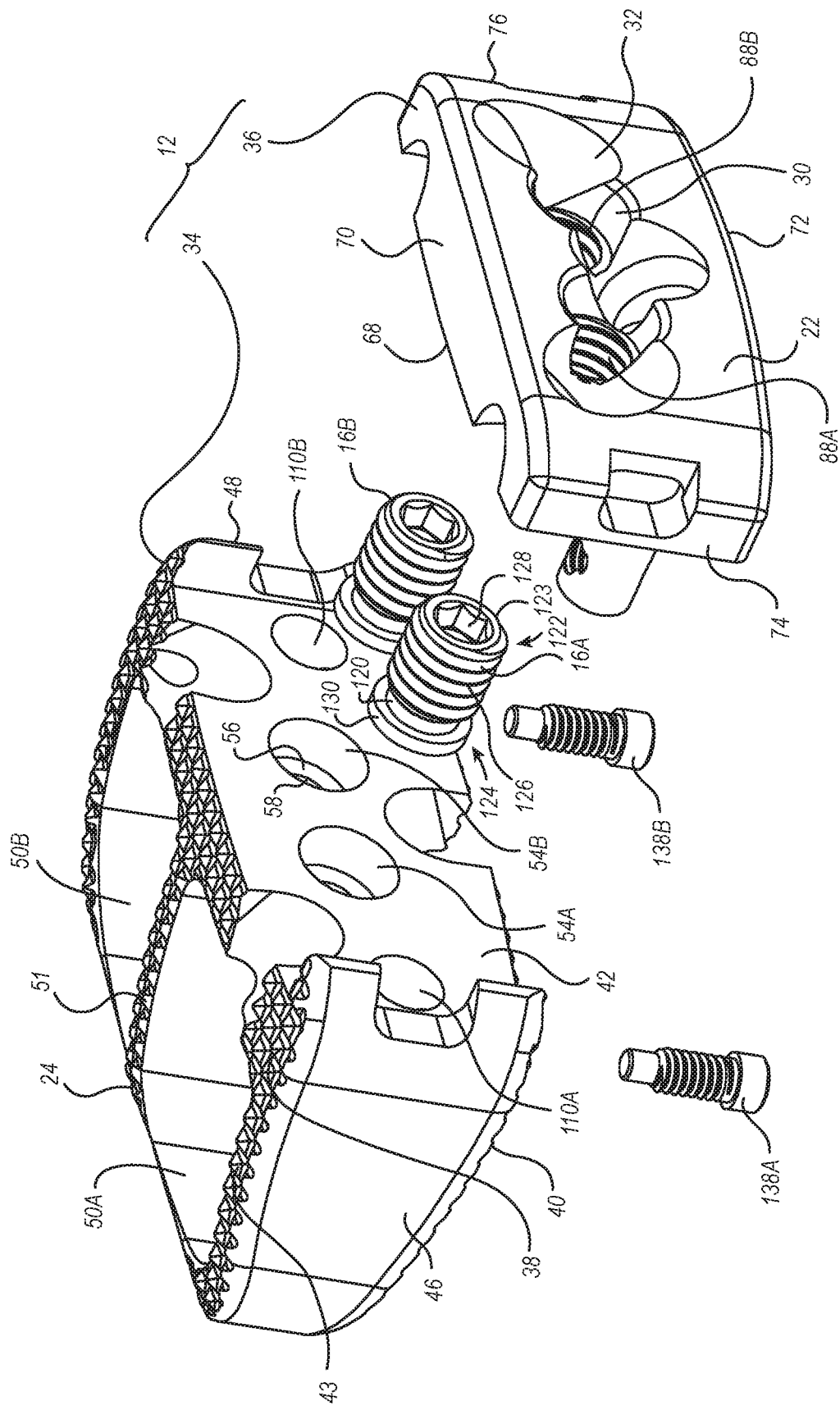
FIG. 2 is a front exploded view of the fusion implant shown in FIG. 1 without the bone screws.

Turning to FIG. 2, fusion spacer 12 is further defined as comprising a body 34 and a faceplate 36 that are selectively coupled together. Body 34 comprises a top surface 38 and an opposing bottom surface 40 that extend between a front face 42 and opposing back face 24 and that also extend between a fist side face 46 and an opposing second side face 48. Again, body 34 is wedge shaped and inwardly tapers from front face 42 to back face 24. Top surface 38 and bottom surface 40 can be linear but typically have a slight convex arch or curve extending from front face 42 to back face 24 and can also have a slight convex arch or curve extending opposing side faces 46 and 48. A plurality of teeth 43 can be formed on top surface 38 and bottom surface 40. Extending through body 34 between top face 38 and bottom face 40 are a pair of cavities 50A and 50B separated by a bridge 51. Cavities 50 are configured to receive a bone growth material, which can be autologous, allograft or synthetic, for use in fusing together adjacent vertebrae. It is appreciated that cavities 50 can be different sizes, shapes, and numbers. For example, 1, 3, 4, or other numbers of cavities can be formed extending through body 34.

Figure 7:
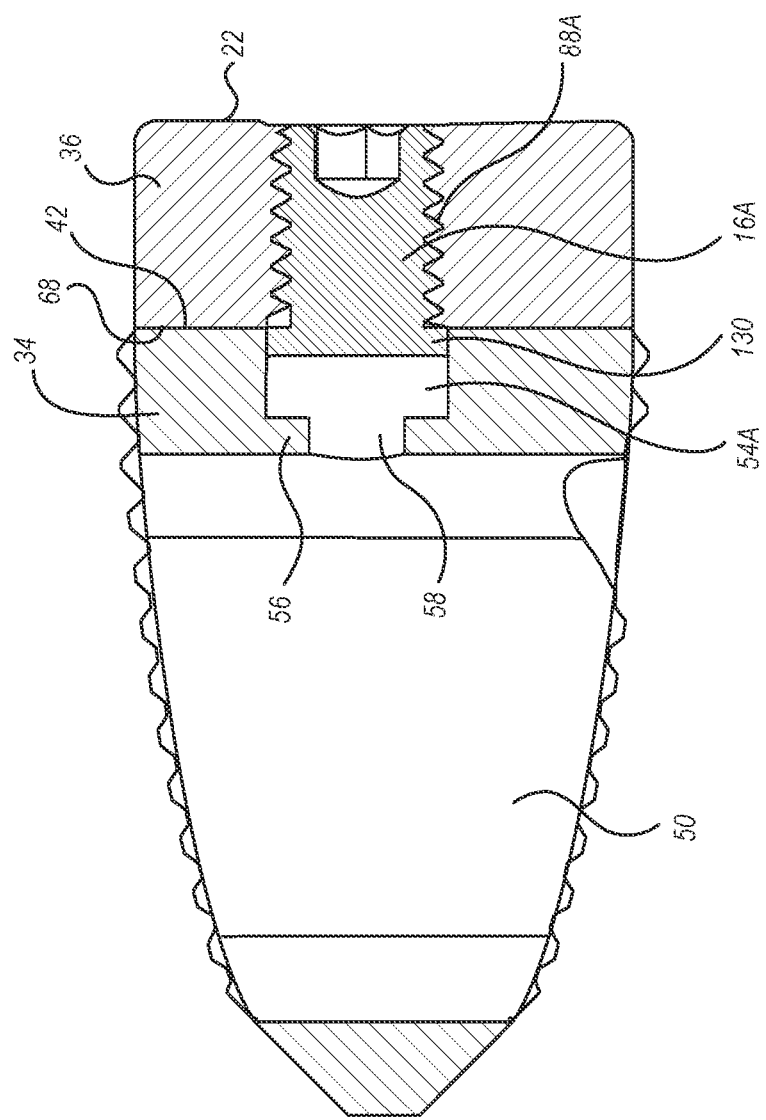
FIG. 7 is a cross sectional side view of the fusion implant shown in FIG. 1 with a locking screw in a retracted position.

Centrally recessed on front face 42 of body 34 is a first access hole 54A and a laterally spaced part second access hole 54B. Access holes 54 are horizontally aligned and can have the same size and configuration. As will be discussed below in greater detail, access holes 54 provide space to enable locking screws 16 to be advanced into body 34. Thus, although access holes 54 are depicted as being cylindrical in shape, other shapes large enough to receive locking screws 16 can also be used. In addition, the two access holes 54A and 54B can be replaced with a single elongated access hole 54 that can receive both locking screws 16A and 16B. Furthermore, the one or two access holes 54 can extend through body 34 to cavities 50 or can or can terminate at a floor formed within body 34 so as to form blind sockets. In the depicted embodiment, access hole 54A and 54B extends to a floor 56. In turn, a constricted opening 58 centrally extends through floor 56 to cavities 50 (FIG. 7).

As will also be discussed below in greater detail, mounting holes 110A and 110B are recessed into front face 42 of body 34 at the opposing ends thereof. Mounting holes 110A and 11B are used for coupling faceplate 36 to body 34 and can comprise either blind sockets or throughways that communicate with cavities 50.

Body 34 is typically molded, milled or otherwise formed from a biocompatible material such as a polyetheretherketone (PEEK) polymer that can be reinforced with a fiber, such as carbon fiber, and/or other additives. In alternative embodiments, body 34 can be formed from medical grade biocompatible metals (such as titanium), alloys, polymers, ceramics, or other materials that have adequate strength.

As depicted in FIG. 2, faceplate 36 includes front face 22 and an opposing back face 68 that both extend between a top face 70 and an opposing bottom face 72 and that extend between opposing side faces 74 and 76. As previously discussed, elongated recess 30 is formed on front face 22 and is partially bounded by interior surface 32. Elongated recess 30 has a longitudinal axis that extends laterally between opposing side faces 74 and 76.

Figure 3:
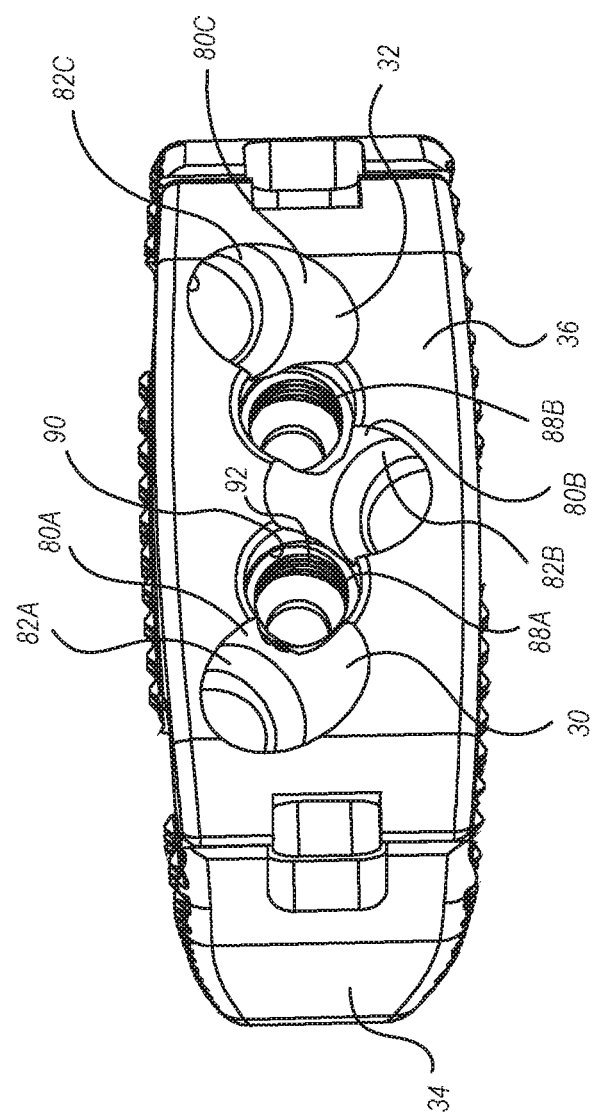
FIG. 3 is a front perspective view of the fusion spacer of the fusion implant shown in FIG. 1.
Figure 4:
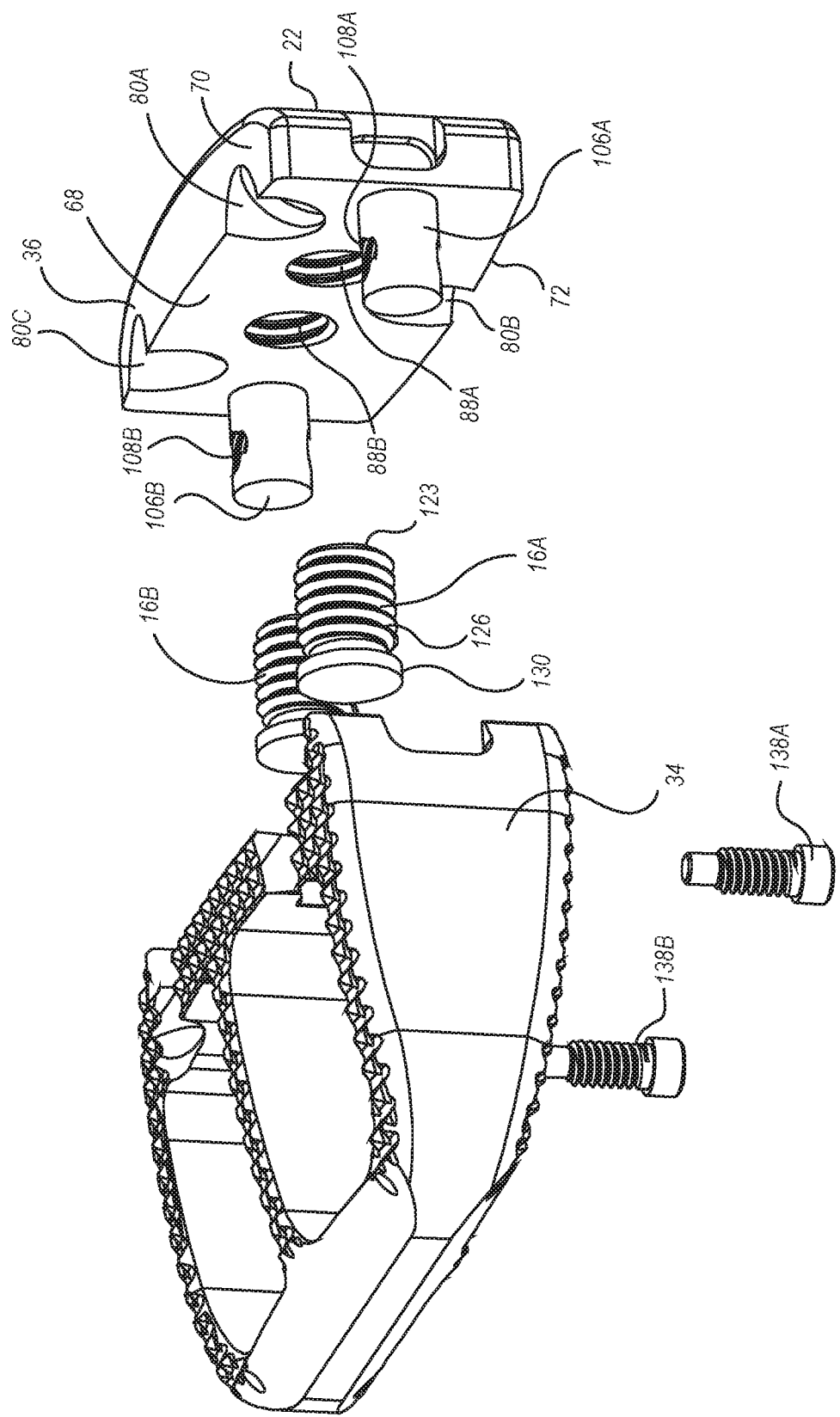
FIG. 4 is a rear exploded view of the fusion implant shown in FIG. 2.
Figure 6:
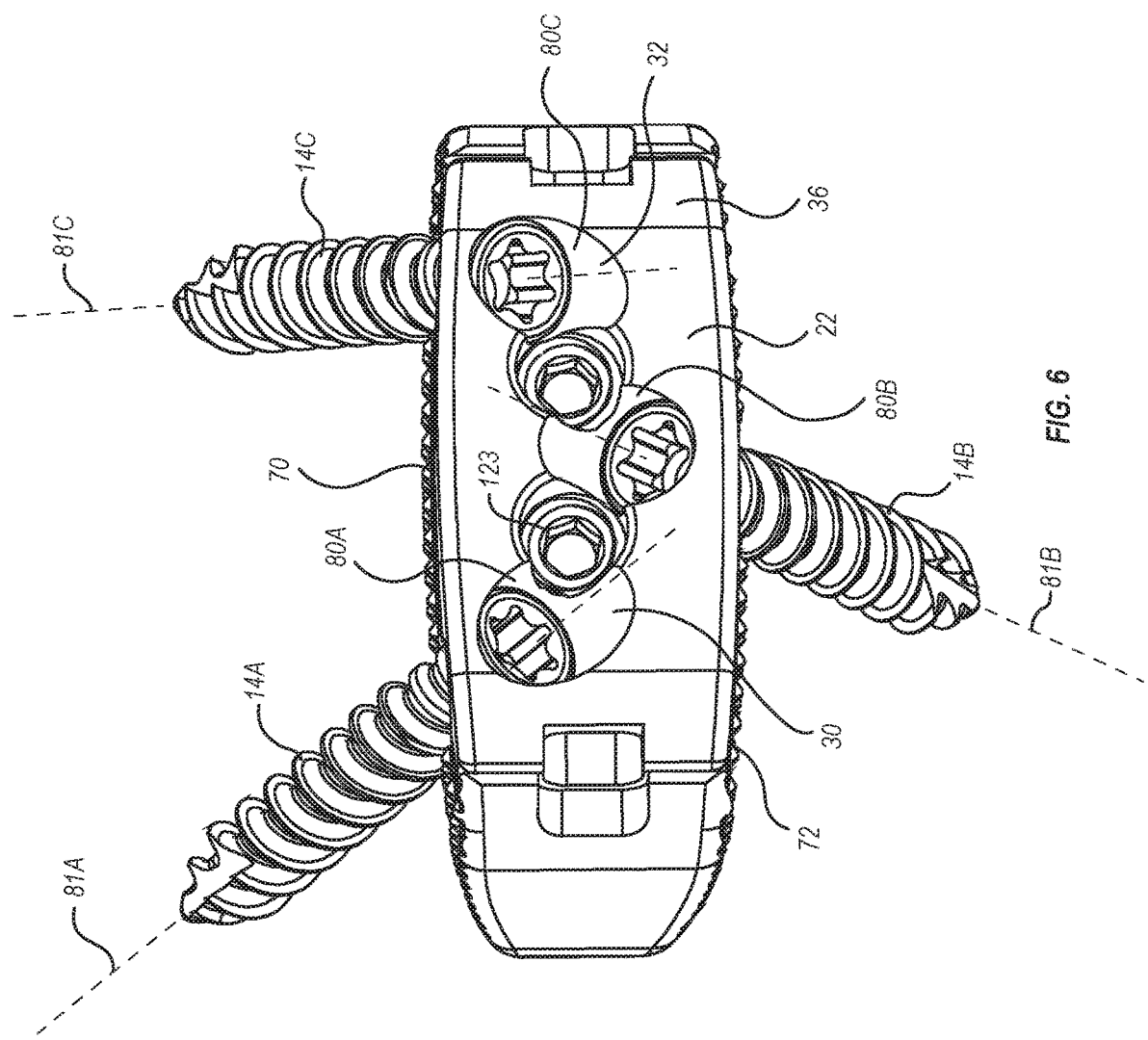
FIG. 6 is a front perspective view of the fusion implant shown in FIG. 1 with the locking screws in an advanced position.

As depicted in FIG. 3, extending through faceplate 36 from interior surface 32 to back face 68 are three screw holes 80A, 80B, and 80C. Screw holes 80A-C are configured to receive bone screws 14A-C (FIG. 1), respectively. As depicted in FIG. 6, screw holes 80A and 80C are disposed at the opposing ends of recess 30 with each having a central longitudinal axis 81A and 81C, respectively, that is sloped. Specifically, axis 81A slopes forward and away from faceplate 36 at a vertical orientation that is downward toward bottom face 72 and a horizontal orientation that is inward toward the center of recess 30. Likewise, axis 81C also slopes forward and away from faceplate 36 at a vertical orientation that is downward toward bottom face 72 and a horizontal orientation that is inward toward the center of recess 30. In this orientation, screw holes 80A and 80C pass out through back face 68 of faceplate 36 so as to partially intersect with top face 70 as shown in FIG. 4.

Returning to FIG. 6, screw hole 80B is centrally located between screw holes 80A and 80C and slopes forward and away from faceplate 36 at a vertical orientation that is upward toward top face 70 and a horizontal orientation that is toward the center of recess 30. As such, screw hole 80B also passes out through back face 68 of faceplate 36 so as to partially intersect with bottom face 72 as shown in FIG. 4. As depicted in FIG. 3, each screw hole 80A-C has an annular, inwardly tapered, chamfer 82A-C, respectively, that is formed at the start of or within each screw hole 80A-C. Each annular chamfer 82 provides an annular seat or shoulder against which the head of each corresponding bone screw 14A-C sits, as discussed below, so that bone screws 14 cannot pass through faceplate 36.

Continuing with FIG. 3, formed on interior surface 32 of recess 30 between first screw hole 80A and second screw hole 80B is a first locking hole 88A. Locking hole 88A extends through faceplate 36 from interior surface 32 to back face 68. At least a portion of locking hole 88A is threaded so that locking screw 16A can be threaded therein. That is, locking hole 88A is bounded by an encircling side surface 90 on which helical threads 92 are formed. A second locking hole 88B is extends through faceplate 36 from interior surface 32 to back face 68 at a location between second screw hole 80B and third screw hole 80C. Second locking hole 88B has the same configuration, orientation and helical threading as first locking hole 88A, as discussed above, and like elements between locking holes 88A and 88B are identified by like reference characters. Second locking hole 88B is configured so that locking screw 16B can be threaded into second locking hole 88B. Locking holes 88A and 88B are position so that when faceplate 36 is coupled with body 34, locking holes 88A and 88B are aligned within access holes 54A and 54B, respectively.

In contrast to being sloped like screw holes 80, locking holes 88 typically extend horizontally into faceplate 36. For example, locking screws 88 can have a central longitudinal axis that is perpendicular to back face 68 of faceplate 32. However, in other embodiments, locking holes 88 and be sloped. In view of the above discussed orientations, axis 81 of each screw hole 80 slopes generally toward one or more of locking holes 88. As discussed below, this orientation enables locking screws 16 disposed within locking holes 88 to block unintended movement of bone screws 14 out of screw holes 80.

Figure 5:
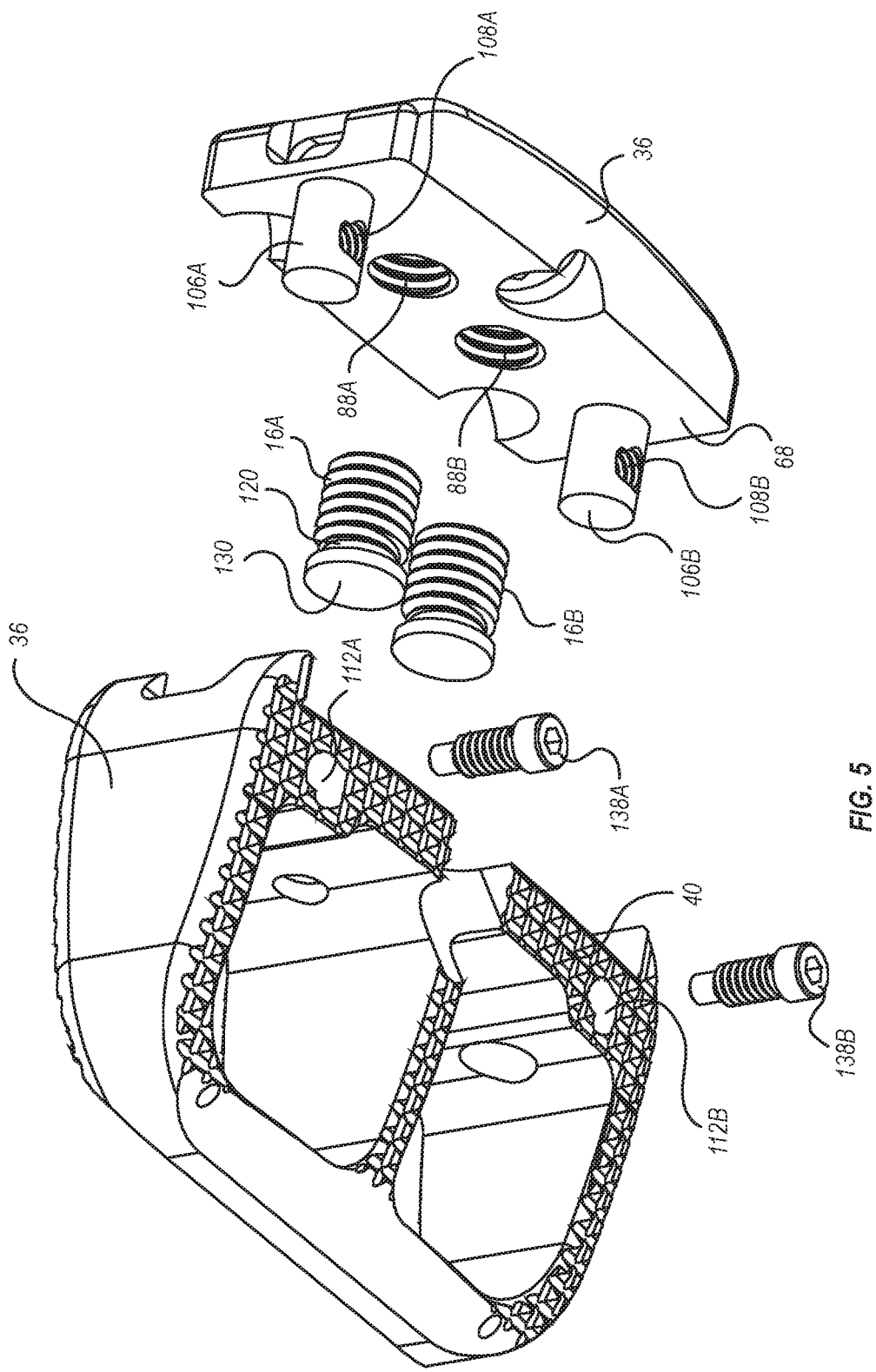
FIG. 5 is a bottom exploded view of the fusion spacer shown in FIG. 4.

As depicted in FIG. 4, to facilitate the coupling of faceplate 36 to body 34, a pair of posts 106A and 106B project from back face 68 of faceplate 36 at the opposing ends thereof. A threaded bore 108A and 108B passes vertically through the side of each post 106A and 106B, respectively. As shown in FIG. 2, mounting holes 110A and 110B formed on front face 42 of body 34 are sized complimentary to posts 106A and B so that posts 106A and B can be received therein. As depicted in FIG. 5, bores 112A and 112B vertically extend up through bottom surface 40 of body 34 so as to intersect with holes 110A and 110B, respectively.

Faceplate 36 is typically molded, milled or otherwise formed from a biocompatible material such as titanium or some other biocompatible metal. Other materials can also be used. Faceplate 36 and body 34 are typically made from different materials but can be made from the same material, such as titanium or other biocompatible metal.

As depicted in FIG. 2, fusion implant 10 also includes first locking screw 16A and second locking screw 16B. Although not required, locking screws 16A and 16B are typically identical. Each locking screw 16 includes a shaft 120 having a first end 122 and an opposing second end 124. Helical threads 126 are formed around shaft 120 along a length of shaft 120 at first end 122. Threads 126 are configured to threaded engage threads 92 of locking holes 88. That is, locking screws 16 can be threaded into locking holes 88. First end 122 of shaft 120 terminates at a terminal end face 123 on which a driver recess 128 is formed. Driver recess 128 is typically in the form of a polygonal socket although other non-circular recesses or slots that can receive a driver for engaging and rotation locking screw 16 can also be used. A stop 130 is formed at second end 124 of shaft 120. At least a portion of stop 130 radially outwardly projects from shaft 120 a distance greater than threads 126. That is, stop 130 is configured so that as first end 122 of shaft 20 is threaded into locking hole 88 from back face 68 of faceplate 36, stop 130 will butt against faceplate 36, e.g., against back face 68, so as to stop locking screws 16 from passing through faceplate 36. Stop 130 can comprise an annular flange or enlarged heard, such as depicted in the drawings. However, stop 130 need not be annular but can comprise one or more fingers, protrusions, or other structures that radially outwardly project from shaft 120.

During assembly, locking screws 16A and B are threaded into locking holes 88A and 88B, respectively, from back face 68 of faceplate 36. Next, posts 106A and 106B of faceplate 36 are received within mounting holes 110A and 110B on body 34. Faceplate 36 and body 34 are pushed together so that back face 68 of faceplate 36 fits flushed against front face 42 of body 34. As faceplate 36 and body 34 are pushed together, second end 124 of locking screws 16A and 16B are received within access holes 54A and 54B, as depicted in FIG. 7. Once faceplate 36 and body 34 coupled together, screws 138A and B (FIG. 5) are passed up through boars 112A and 112B, respectively, and are threaded into boars 108A and 108B extending through posts 106A and 106B of faceplate 36, thereby securing faceplate 36 to body 34. It is appreciated that other methods can also be used to secure faceplate 36 to body 34. For example, screws could be advanced through holes in faceplate 36 and threaded directly into body 34, thereby securing faceplate 36 to body 34. In this alternative embodiment, posts 106 and holes 110 could be retained or eliminated. Other methods can also be used.

Figure 9A:
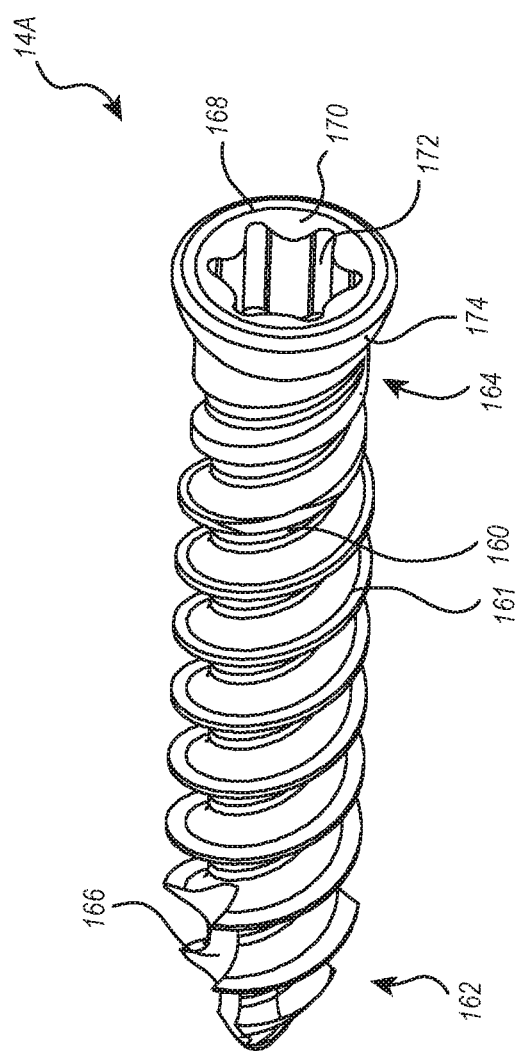
FIG. 9A is a front perspective view of a bone screw of the fusion implant shown in FIG. 1.
Figure 9B:
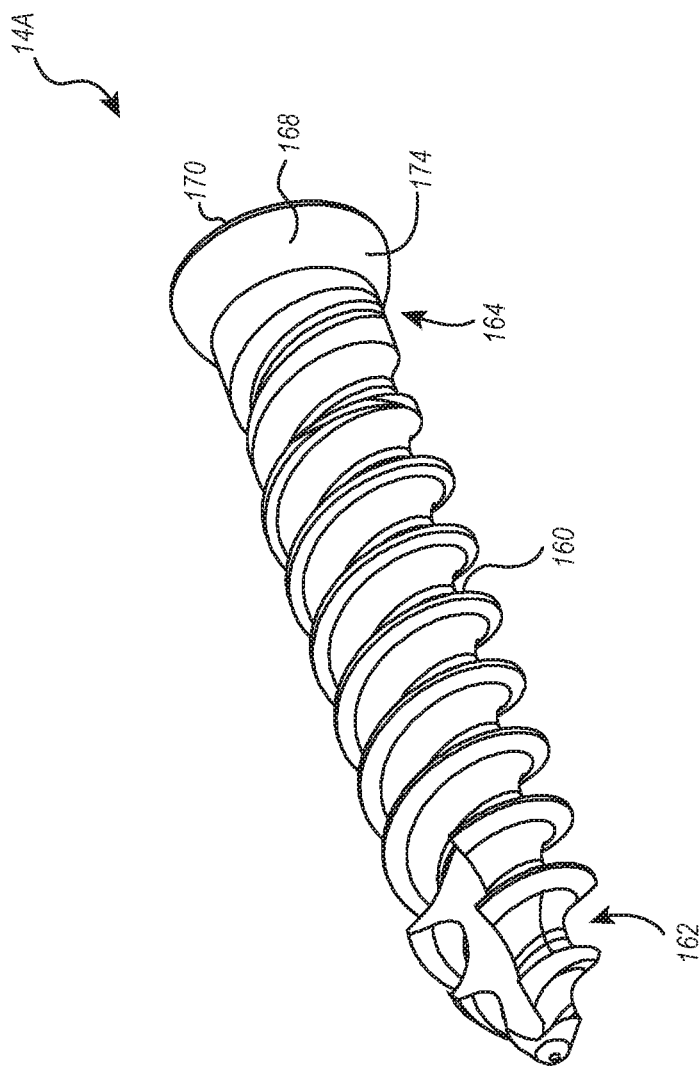
FIG. 9B is a rear perspective view of the bone screw shown in FIG. 9A.

Turning to FIGS. 9A and 9B, each bone screw 14 includes a shaft 160 having a helical thread 161 extending between a first end 162 and an opposing second end 164. First end 162 is tapered and can have one or more cutting slots 166 formed through threads 161 at first end 162. An enlarged head 168 is formed at second end 164 of shaft 160. Head 168 terminates at a terminal end face 170 having a driver recess 172 formed therein. Although driver recess 172 typically comprise a polygonal socket, driver recess 172 can comprise any size or shape of recess or slot that functions to receive a driver for engaging and rotating bone screw 14. Head 168 has an annular tapered surface 174 that outwardly flares from second end 164 of shaft 160 to terminal end face 170. As previously discussed, bone screws 14 are sized and configured to pass through screw holes 80 for threading into bone, such as adjacent vertebrae, to thereby securely fix fusion implant 10 between adjacent vertebrae. As bone screws 14 are passed through screw holes 80, tapered surface 174 of bone screws 14 seats against annular chamfers 82 of faceplate 36 (FIG. 3) so as to prevent bone screws 14 from passing through faceplate 36.

Figure 8:
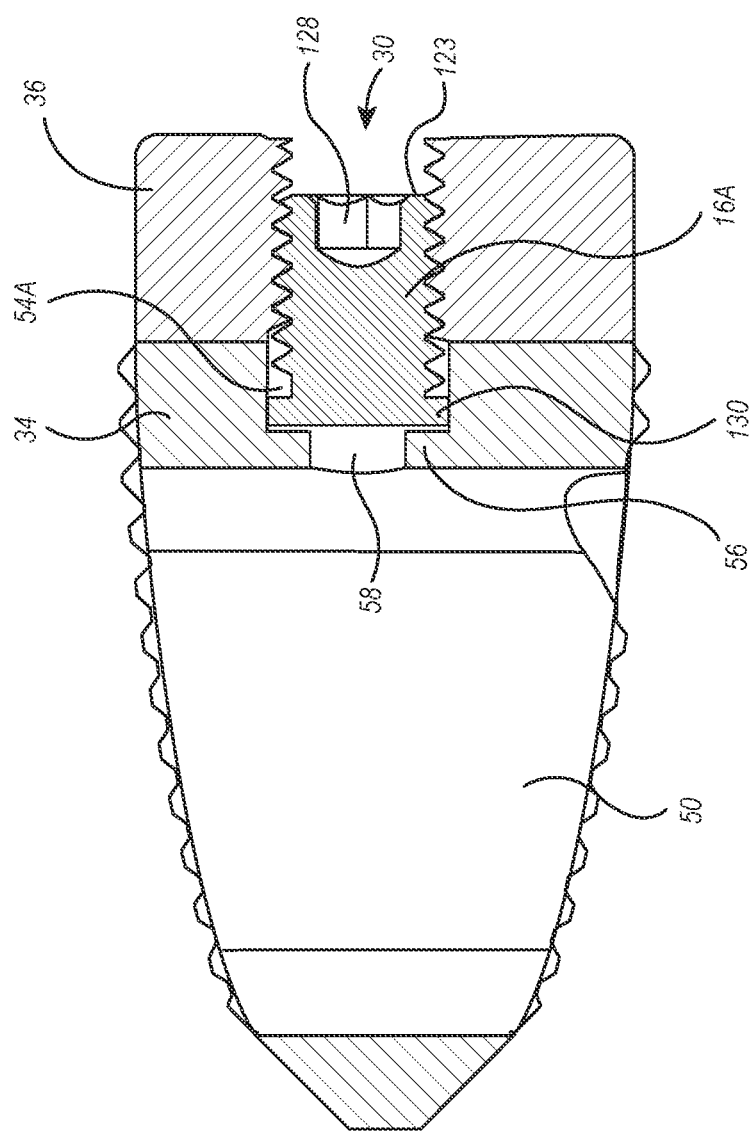
FIG. 8 is a cross sectional side view of the fusion implant shown in FIG. 1 with a locking screw in an advanced position.

As previously mentioned, with fusion implant 10 fully assembled, locking screws 16 are used to prevent bone screws 14 from unintentionally moving or backing out of fusion spacer 12. That is, by inserting a driver into driver recess 128 of locking screws 16, the driver can be used to rotate locking screws 16 relative to faceplate 32 and thereby move locking screws 16 relative to faceplate 32 between an advanced position and a retracted position. In the advanced position, as depicted in FIGS. 6 and 8, locking screws 16 are screwed or threaded sufficiently far into faceplate 36 so that bone screws 14A-C can be freely advanced into or removed from screw holes 80A-C, respectively, without interference or obstruction by locking screws 16. In one embodiment, locking screws 16 are advanced until stops 130 butt against floor 56 of each access hole 54. Floor 56 thus functions to both prevent locking screws 16 from disengaging with faceplate 36 and identify when locking screws 16 are in the advanced position. Although not always required, terminal end face 123 of locking screws 16 is typically flush with or recessed into interior surface 32 (FIG. 1) of recess 30 when locking screws 16 are in the advanced position. Terminal end face 123 of locking screws 16 is also typically inwardly spaced apart from front face 22 of faceplate 36 when locking screws 16 are in the advanced position.

Once bone screws 14 are properly positioned within screw holes 82, locking screws 16 can be rotated by a driver so as to move locking screws 16 from the advanced position to the retracted position, as shown in FIGS. 1 and 7. In the retracted position, locking screws 16 are position to obstruct the removal of bone screws 14 from screw holes 80. That is, because of the angled orientation of screw holes 18, if bone screws 14 try to back out of screw holes 80 with locking screws 16 in the retracted position, bone screws 14 run into locking screws 16 which prevents bone screws 14 from backing out of fusion spacer 12 and thus also prevents any significant movement of bone screws 14. In one embodiment, locking screws 16 function to decrease the size of the entrance of screw holes 80 when in the retracted position so that bone screws 14 can no longer pass out of screw holes 80. More specifically, with locking screws 16 in the retracted position, bone screw 14A is blocked from passing out of screw hole 80A by locking screw 16A while bone screw 14C is blocked from passing out of screw hole 80C by locking screw 16B. Bone screw 14B is blocked from passing out of screw hole 80B by both locking screw 16A and locking screw 16B.

In one embodiment, stop 130 of locking screws 16 butts against back face 68 of faceplate 32 when locking screws 16 are in the retracted position. Stop 130 thus functions to enable locking screws 16 to firmly bias against faceplate 32 so that bone screws 16 can be rigidly fixed in place when in the retracted position. Stops 130 also prevent bone screws 16 from disengaging from faceplate 32 as bone screws 16 are advanced into the retracted position and identify when bone screws 16 are in the retracted position. Terminal end face 123 of locking screws 16 can be flush with, recessed into or project out of front face 22 of faceplate 36 when locking screws 16 are in the retracted position.

If it was subsequently desired to remove bone screws 14 from fusion spacer 12, locking screws 16 can again be moved back to their advanced position. Bone screws 14 can then be removed from screw holes 80 without obstruction by locking screws 16.

Different embodiments of the present invention provided a number of unique advantages. For example, the present invention provides an easy mechanism for locking the bone screws to the fusion spacer so that the bone screws do not unintentionally back out of the fusion spacer or move beyond a tolerated amount. The inventive spinal implant is effective and easy to use. Furthermore, the present invention provides an easy mechanism for moving the locking screws without risk of them disengaging. Different embodiments of the present invention also have other benefits.

The present invention may be embodied in other specific forms without departing from its spirit or essential characteristics. For example, the placement, orientation and number of bone screws and locking screws can be modified as needed. For example, in one embodiment, only two bone screws may be used and thus only one locking screw may be required. Furthermore, in one embodiment floors 56 (FIG. 7) can be removed so that access holes 54 extend unrestricted to cavities 50. Locking screws 16 could then be advanced into access holes 54 and into locking holes from cavities 50. In this embodiment, faceplate 36 and body 34 could be formed as a single, integral, continuous member forming fusion spacer 12 as opposed to two separate members that are connected together.

The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:
1. An interbody spinal fusion implant comprising:
   a fusion spacer having a top surface and an opposing bottom surface that extend between a front face and an opposing back face, a recess being formed on the front face and being at least partially bounded by an interior surface, a first screw hole passing through the interior surface of the recess;
a first bone screw being received within the first screw hole; and
a first locking screw at least partially disposed within the recess of the fusion spacer, the first locking screw comprising a threaded shaft and being threadedly engaged with the fusion spacer, the first locking screw being movable between an advanced position wherein the first locking screw is advanced into fusion spacer and a retracted position wherein the first locking screw is partially retracted out of the fusion spacer relative to the advanced position, wherein when the first locking screw is in the advanced position the first bone screw can be freely removed from the first screw hole and when the first locking screw is in the retracted position the threaded shaft of the first locking screw blocks removal of the first bone screw from the first screw hole,
wherein the first locking screw comprises:
the threaded shaft extending between a first end and an opposing second end, the first end terminating at a terminal end face, the threaded shaft being threaded into a first locking hole formed on the fusion spacer;
a driver recess formed on the terminal end face at the first end of the threaded shaft; and
an enlarged stop formed on the second end of the threaded shaft.

2. The interbody spinal fusion implant as recited in claim 1, further comprising:
a second screw hole passing through the interior surface of the recess at a location spaced apart from the first screw hole; and
a second bone screw being received within the second screw hole, wherein when the first locking screw is in the advanced position, the second bone screw can be freely removed from the second screw hole, and when the first locking screw is moved to the retracted position, the first locking screw blocks removal of the first bone screw from the first screw hole and blocks removal of the second bone screw from the second screw hole.

3. The interbody spinal fusion implant as recited in claim 1, wherein the fusion spacer comprises:
a body having a top surface and an opposing bottom surface that extend between a front face and an opposing back face; and
a face plate having a top surface and an opposing bottom surface that extend between a front face and an opposing back face, the back face of the face plate being secured to the front face of the body, wherein the recess is formed on the front face of the face plate and the first locking hole extends through the face plate from the interior surface of the recess.

4. The interbody spinal fusion implant as recited in claim 3, wherein the stop comprises an annular flange outwardly projecting from the second end of the threaded shaft and disposed between the body and the face plate, the flange being sized so that the flange cannot pass through the first locking hole.

5. The interbody spinal fusion implant as recited in claim 4, wherein the annular flange has a diameter that comprises a maximum diameter of the first locking screw.

6. The interbody spinal fusion implant as recited in claim 3, wherein when the first locking screw is in the retracted position, the terminal end face of the first locking screw is flush with the front face of the face plate or is disposed within the recess on the front face.

7. The interbody spinal fusion implant as recited in claim 1, wherein the driver recess comprises a polygonal socket recessed into the terminal end face of the threaded shaft.

8. The interbody spinal fusion implant as recited in claim 1, wherein the threaded shaft comprises a thread that extends to the terminal end face.

9. The interbody spinal fusion implant as recited in claim 1, wherein the terminal end face of the threaded shaft is circular.

10. An interbody spinal fusion implant comprising:
a body having a top surface and an opposing bottom surface that extend between a front face and an opposing back face;
a face plate secured to the front face of the body, the face plate having a top surface and an opposing bottom surface that extend between a front face and an opposing back face, a recess being formed on the front face of the face plate and being at least partially bounded by an interior surface, a first screw hole and a spaced apart first locking hole passing through the face plate from interior surface of the recess; and
a first locking screw comprising:
a shaft extending between a first end and an opposing second end and having a thread formed along at least a portion of a length thereof, the first end of the shaft terminating at a terminal end face, the shaft being threaded into the first locking hole;
a driver recess formed on the terminal end face at the first end of the threaded shaft and being accessible from the front face of the face plate; and
a stop formed on the second end of the shaft, the stop having a diameter that comprises a maximum diameter of the first locking screw.

11. The interbody spinal fusion implant as recited in claim 10, wherein the stop cannot pass through the first locking hole.

12. The interbody spinal fusion implant as recited in claim 10, wherein the stop is disposed within the body.

13. The interbody spinal fusion implant as recited in claim 10, wherein the first locking screw is movable between an advanced position wherein a first bone screw can be freely advanced into the first screw hole and a retracted position wherein a first bone screw disposed within the first screw hole would be blocked by the first locking screw from being removed from the first screw hole.

14. The interbody spinal fusion implant as recited in claim 13, further comprising a first bone screw received within the first screw hole, the first bone screw being blocked from removal by the first locking screw when the first locking screw is in the retracted position.

15. The interbody spinal fusion implant as recited in claim 14, further comprising:
a second screw hole passing through the face plate from interior surface of the recess; and
a second bone screw received within the second screw hole, the second bone screw being blocked from removal by the first locking screw when the first locking screw is in the retracted position.

16. The interbody spinal fusion implant as recited in claim 14, wherein the first bone screw and the second bone screw can be freely removed from the first screw hole and the second screw hole, respectively, when the first locking screw is advanced into the advanced position.

17. The interbody spinal fusion implant as recited in claim 13, wherein when the first locking screw is in the advanced position, the terminal end face of the first locking screw is flush with the front face of the face plate or is disposed within the recess on the front face of the face plate.

18. The interbody spinal fusion implant as recited in claim 10, wherein the stop comprises an annular flange outwardly projecting from the second end of the shaft, wherein the flange being sized so that the flange cannot pass through the first locking hole.

19. The interbody spinal fusion implant as recited in claim 10, wherein the driver recess comprises a polygonal socket recessed into the terminal end face of the shaft.

20. The interbody spinal fusion implant as recited in claim 10, wherein the thread extends to the terminal end face of the shaft.

21. The interbody spinal fusion implant as recited in claim 10, wherein the shaft at the terminal end face has an outer perimeter that is circular.

22. The interbody spinal fusion implant as recited in claim 10, wherein the shaft extending from the stop to the terminal end face has a cylindrical configuration.

* * * * *